(12) United States Patent
Sivak et al.

(10) Patent No.: US 8,838,263 B2
(45) Date of Patent: Sep. 16, 2014

(54) PATIENT SPECIFIC ANKLE-FOOT ORTHOTIC DEVICE

(75) Inventors: Mark L. Sivak, Boston, MA (US); Richard G. Ranky, Ridgewood, NJ (US); Joseph A. DiPisa, Wyckoff, NJ (US); Alyssa Leigh Caddle, South Boston, MA (US); Kara Lyn Gilhooly, Watertown, MA (US); Lauren Chiara Govoni, Quincy, MA (US); Seth John Sivak, Cambridge, MA (US); Michael Lancia, Wakefield, RI (US); Paolo Bonato, Somerville, MA (US); Constantinos Mavroidis, Arlington, MA (US)

(73) Assignees: Spaulding Rehabilitation Hospital Corporation, Boston, MA (US); Northeastern University, Boston, MA (US); Technest Holding, Inc., Bethesda, MD (US)

( * ) Notice: Subject to any disclaimer, the term of this patent is extended or adjusted under 35 U.S.C. 154(b) by 687 days.

(21) Appl. No.: 12/472,984

(22) Filed: May 27, 2009

(65) Prior Publication Data

US 2009/0306801 A1 Dec. 10, 2009

Related U.S. Application Data

(63) Continuation-in-part of application No. PCT/US2007/024520, filed on Nov. 27, 2007.

(60) Provisional application No. 60/861,107, filed on Nov. 27, 2006.

(51) Int. Cl.
*A61F 2/00* (2006.01)
*A61F 2/64* (2006.01)
*A61F 2/68* (2006.01)
*A61F 2/74* (2006.01)
*A61F 5/01* (2006.01)

(52) U.S. Cl.
CPC ............. *A61F 5/0111* (2013.01); *A61F 5/0113* (2013.01)

USPC ............. 700/118; 700/98; 700/105; 700/117; 700/119; 700/120; 623/27; 623/47; 623/53; 623/59; 623/61

(58) Field of Classification Search
USPC .......... 700/98, 117–120, 163; 623/27, 47, 53, 623/59, 61
See application file for complete search history.

(56) References Cited

U.S. PATENT DOCUMENTS 5,092,022 A * 3/1992 Duret ........................... 29/896.1
5,432,703 A * 7/1995 Clynch et al. ................. 700/163

(Continued)

OTHER PUBLICATIONS

De Laurentis, Kathryn F., Mavroidis, Constantinos; "Rapid fabrication of a non-assembly robotic hand with embedded components"; Assembly Automation; 2004, vol. 24(4): 394-405.

(Continued)

*Primary Examiner* — Mohammad Ali
*Assistant Examiner* — Jennifer L Norton
(74) *Attorney, Agent, or Firm* — Wilmer Cutler Pickering Hale and Dorr LLP

(57) ABSTRACT

The unique advantages of computer-controlled fabrication of a patient-specific orthotic device using an automated fabrication machine capable of following computer instructions to create 3D surface contours and new developments in non-invasive three-dimensional (3D) scanning have made it possible to acquire digital models of freeform surfaces such as the surface anatomy of the human body and to then fabricate such a patient-specific device with high precision. Such a patient-specific device brings significant improvement in patient-specific fit, comfort, and function of medical devices (and, in particular, to orthoses that require a close fit to the wearer's body to act effectively). The combination of these two technologies is ideally suited for the development of patient-specific orthotic devices.

A patient specific ankle-foot orthotic device using this technology is disclosed. This exemplary device is used to help stabilize the ankle-foot region, for example, in patients with impaired gait.

17 Claims, 7 Drawing Sheets

(56) References Cited

U.S. PATENT DOCUMENTS

| | | | |
|---|---|---|---|
| 5,448,489 A * | 9/1995 | Reuben | 700/163 |
| 5,487,012 A | 1/1996 | Topholm et al. | |
| 5,522,402 A * | 6/1996 | Cooley | 600/595 |
| 6,379,393 B1 * | 4/2002 | Mavroidis et al. | 623/25 |
| 6,594,539 B1 | 7/2003 | Geng | |
| 6,920,414 B2 * | 7/2005 | Tøpholm | 703/1 |
| 6,968,075 B1 * | 11/2005 | Chang | 382/154 |
| 6,978,188 B1 * | 12/2005 | Christensen | 700/118 |
| 7,065,232 B2 | 6/2006 | Geng | |
| 7,099,732 B2 | 8/2006 | Geng | |
| 7,340,316 B2 * | 3/2008 | Spaeth et al. | 700/98 |
| 7,346,418 B2 * | 3/2008 | Lowe | 700/118 |
| 7,356,379 B2 * | 4/2008 | Slemker et al. | 700/118 |
| 7,396,337 B2 * | 7/2008 | McBean et al. | 601/5 |
| 7,571,018 B2 * | 8/2009 | Roth et al. | 700/98 |
| 7,578,799 B2 * | 8/2009 | Thorsteinsson et al. | 602/5 |
| 7,707,751 B2 * | 5/2010 | Avent et al. | 36/150 |
| 7,794,505 B2 * | 9/2010 | Clausen et al. | 623/24 |
| 8,005,651 B2 * | 8/2011 | Summit et al. | 703/1 |
| 8,100,692 B2 * | 1/2012 | Diangelo et al. | 433/213 |
| 8,118,878 B2 * | 2/2012 | Nuffer et al. | 623/47 |
| 8,142,370 B2 * | 3/2012 | Weinberg et al. | 601/5 |
| 8,246,558 B2 * | 8/2012 | Barrera et al. | 602/16 |
| 8,483,863 B1 * | 7/2013 | Knox | 700/118 |
| 8,500,668 B2 * | 8/2013 | Siegler et al. | 602/23 |
| 8,538,570 B2 * | 9/2013 | Stanhope et al. | 700/98 |
| 8,551,029 B1 * | 10/2013 | Herr et al. | 602/16 |
| 8,565,909 B2 * | 10/2013 | Bickel et al. | 700/98 |
| 2002/0015934 A1 | 2/2002 | Rubbert et al. | |
| 2002/0059042 A1 * | 5/2002 | Kacyra et al. | 702/152 |
| 2004/0196995 A1 * | 10/2004 | Martin Roth et al. | 381/322 |
| 2005/0015172 A1 | 1/2005 | Fried et al. | |
| 2005/0019732 A1 * | 1/2005 | Kaufmann et al. | 433/213 |
| 2005/0088435 A1 | 4/2005 | Geng | |
| 2005/0089822 A1 | 4/2005 | Geng | |
| 2005/0096576 A1 * | 5/2005 | Castro | 602/27 |
| 2005/0142517 A1 * | 6/2005 | Frysh et al. | 433/173 |
| 2006/0023228 A1 | 2/2006 | Geng | |
| 2006/0094951 A1 * | 5/2006 | Dean et al. | 600/407 |
| 2006/0283243 A1 * | 12/2006 | Peterson | 73/172 |
| 2007/0016323 A1 | 1/2007 | Fried | |
| 2007/0118055 A1 * | 5/2007 | McCombs | 600/587 |
| 2007/0265727 A1 * | 11/2007 | Bae et al. | 700/182 |
| 2008/0292179 A1 * | 11/2008 | Busch | 382/154 |
| 2009/0042167 A1 * | 2/2009 | Van Der Zel | 433/215 |
| 2009/0298017 A1 * | 12/2009 | Boerjes et al. | 433/214 |

OTHER PUBLICATIONS

Pages from the website http://www.idea.be/measuring_modelling_modeling_manufacturing.aspx (10 pages).

Dolenc, A., Dr.; "An Overview of Rapid Prototyping Technologies in Manufacturing"; Helsinki University of Technology; 1994; 1-23.

Kai, Chua Chee, et al., "Facial prosthetic model fabrication using rapid prototyping tools"; Integrated Manufacturing Systems; 2000; 11(1): 42-53.

Chu, T.M., et al.; "Three-dimensional finite element stress analysis of the polypropylene, ankle-foot orthosis: static analysis"; Med. Eng. Phys; 1995; 17(5): 372-379.

Hieu, L.C. and Slatov, N.; "Medical rapid prototyping applications and methods"; Assembly Automation; 2005; 25(4): 284-292.

Zollikofer C. and Ponce De Leon, M.S.; "Tools for Rapid Prototyping in the Biosciences"; IEEE Computer Graphics and Applications; 1995; 48-55.

Crawford, R.H. and Beaman, J.J.; "Solid Freeform Fabrication"; IEEE Spectrum; 1999; 36(2): 34-43.

Laliberte, T., et al.; "Practical Prototyping: A Rapid Prototyping Framework for Fast and Cost-Effective Design of Robotic Mechanism Prototypes"; IEEE Robotic & Automation Magazine; 2001; 8(3): 43-52.

Vergeest J.S.M. and Tangelder, J.W.H.; "Robot Machines Rapid Prototype"; Industrial Robot; 1996; 23(5): 17-20.

Potamianos, P., et al.; "Rapid prototyping for orthopaedic surgery"; Proc Instn Mech Engrs; 1998; 212(H): 383-393.

Muller, Adolf, et al.; "The application of Rapid Prototyping Techniques in Cranial Reconstruction and Preoperative Planning in Neurosurgery"; The Journal of Craniofacial Surgery; (2003); 14(6): 899-904.

Noorani, R.; "Medical Applications of Rapid Prototyping"; John Wiley & Sons, Inc., Hoboken; (2006); pp. 269-288.

Sinn, D.P., et al.; "Stereolithography for Craniofacial Surgery"; The Journal of Craniofacial Surgery; (2006); 17(5): 869-875.

Sammarco, J. and Hockenbury, R.T.; "Biomechanics of the Foot and Ankle"; Basic Biomechanics of the Musculoskeletal System; (2001); Chapter 9; 222-255.

Diez, J.; "Advantages of Using Additive Fabrication"; Design for Additive Fabrication Building Miniature Robotic Mechanisms; (2001); 58-62.

Van Dijk, M., et al.; "Polyurethane Real-Size Models Used in Planning Complex Spinal Surgery"; SPINE; (2001); 26: 1920-1926.

Winter, D.A.; "Kinetics: Forces and Moments of Force"; Biomechanics and Motor Control of Human Movement; (1990); $2^{nd}$ Ed. New York: A Wiley-Interscience Publication; pp. 75-89.

Winter, D.A.; "Force-Velocity Characteristics"; Biomechanics and Motor Control of Human Movement; (1990); $2^{nd}$ Ed. New York: A Wiley-Interscience Publication; pp. 177-180.

\* cited by examiner

PATIENT SPECIFIC ANKLE-FOOT ORTHOTIC DEVICE

CROSS REFERENCE TO RELATED APPLICATIONS

This application is a continuation-in-part of PCT International Application No. PCT/US2007/024520 filed on Nov. 27, 2007, which claims the priority of U.S. Provisional Application No. 60/861,107 filed on Nov. 27, 2006, both of which are hereby incorporated by reference herein.

STATEMENT REGARDING FEDERALLY SPONSORED RESEARCH OR DEVELOPMENT

N/A

BACKGROUND OF THE INVENTION

Ankle-foot orthotic (AFO) devices are designed to correct gait impairments for patients by stabilizing and securing the ankle-foot complex during gait. AFOs can be required for patients affected by a wide range of conditions including direct injury to the dorsiflexors, the common peroneal, the sciatic nerves, or the neural pathways that supply them. AFOs are also used to treat gait impairments resulting from conditions such as cerebral palsy, multiple sclerosis, or scoliosis, and are also common among subjects post-stroke who cannot properly dorsiflex their ankle or extend their toes. The patient, in rehabilitation therapy, uses such an orthotic device to ambulate daily, so it is essential that its shape maintains a high level of comfort while its material properties provide the necessary stiffness and support based on the patient's needs. However, AFOs are not created to fit the anatomy of a specific subject. Size ranges are built as an approximate fit for an anthropomorphic range of ankle-foot anatomy and, thus, are less likely to fit a particular subject comfortably. Standard models do not provide individualized comfort or support to the wearer. Considering the unique gait conditions and surface anatomy of each patient, an easy way to obtain custom made AFOs is required.

The current process to fit a custom AFO, which is depicted in FIGS. 1A-1F, is a laborious and time-intensive manual process performed by skilled orthotists. Once the orthotist has performed gait and muscle evaluation to determine the configuration and orientation of the subject's anatomy for corrective measures, the form of the device is captured by wrapping a sock around and then casting the leg (FIG. 1A). Markings are drawn onto the sock surface at key locations, which instruct technicians later on as to the corrective modifications that are necessary. After the cast has set (FIG. 1B), it is cut away along the anterior contour, in line with the tibia (FIG. 1C). The open edge of the cast is filled and plaster is poured into the leg cavity. During casting the original markings on the sock can slide along the surface up to ½" away, introducing fabrication tolerances. This also requires the technician to have some fundamental anatomical and kinematic gait understanding to scrutinize the locations of the markings. Depending on the corrective measures desired, surface material is removed or added (FIGS. 1D, 1E) and thermoplastic is vacuum formed around the modified leg bust (FIG. 1F). Any further adjustments made to customize the standard orthotic device are carried out in a qualitative manner, so both comfort and function can remain sub-optimal.

An improved technique for fabricating a patient-specific orthotic device would provide the orthopedic specialist with the ability to obtain excellent comfort for a patient and also would allow for customized changes in the standard design to support the anatomy of the patient in the anatomical regions where such support would be most beneficial.

BRIEF SUMMARY OF THE INVENTION

The invention is directed to a method for the rapid fabrication of all or a part of an orthotic device specific to an individual patient (or other general wearer), e.g., the fabrication of an ankle-foot orthotic (AFO) device or other medical device requiring a patient-specific anatomical fit and function. The method of the invention uses 3D scanning technology to obtain a digital model, e.g., of the ankle-foot area of a patient; then modifies the digital model to fit the patient's needs, e.g., by surface expansion, contraction, thickening and smoothing contours, etc.; and finally fabricates the model using an automated fabrication machine capable of following computer instructions to create 3D surface contours.

Appropriate fabrication techniques for creating 3D surface contours include, for example, layered manufacturing techniques (also known at the present time as rapid prototyping/rapid manufacturing or fabrication/layered prototyping, etc.), such as stereolithography; fused deposition modeling; selective laser sintering; and CNC milling to produce an orthotic device that will fit the individual patient with greatly reduced lead time while, at the same time, providing the ability to keep a quantitative digital record (47) of the patient and his/her device, as shown in FIG. 4.

By using one of these computer controlled techniques in the fabrication step of the method of the invention, it is also possible to design into the custom orthotic device the positions for additional components, e.g., electronic components, which may be embedded in the device during the build process, or post-production if preferred. The steps of this method can all be carried out for an individual patient by a human (manual operation), by a computer & robot (automatic operation) or by a combination of both, with some automated and some manual operations. The steps of the method can also be used to fabricate a portion of the desired orthotic device, and the method of the invention can be supplemented by steps according to the prior art in order to complete the construction of the device.

Specifically, in one embodiment, the method comprises: a) obtaining multiple, precise 3D scans of a patient's body part, e.g., ankle and foot, (via, e.g., MRI or CT) using, e.g., Face-Cam or any scanner that is capable of creating a full 3D point cloud of a body part, preferably with all contours greater than 0.5 mm. This device may be handheld by the medical practitioner (e.g., a polhemus scanner), statically mounted in a facility (e.g., MRI, CT scanner), or may be mounted on an automated device (e.g., robotic armature, exoskeleton, or guide track) and controlled real-time by the practitioner or by an automated routine; b) using software (e.g., RapidForm, Meshlab, Geomagic Studio, Polyworks) to clean the data (the full 3D point cloud) by removing extraneous points, smoothing the contours of the surfaces and merging individual scans into a complete model; c) modifying/manipulating the surface contours of the digital model according to the wearer and medical practitioner's requirements to combine the images into the desired orthotic device (with or without designing in positions for embedded components); d) converting the model data into CAD/CAM format (create a .STL file); and e) inputting the build geometry .STL file into a machine capable of some type of 3D computer controlled fabrication technique (e.g., layered fabrication (for example, stereolithography), selective laser sintering, fused deposition modeling, shape deposition modeling, polymer jetting, CNC milling) along with the appropriate materials (e.g., photosensitive resin polymer, nylon powder, polypropylene) to produce the desired orthotic device (in pieces if necessary). These software operations can be performed by a medical assistant manually on the computer or by programming the specifications for the orthotic device (e.g., selecting type, size, material, geometry, thickness, etc.) for automated data cleanup and preparation. Referring to FIG. 4, after the fabrication stage, preparing the orthotic device for use with a human patient (46) may require additional steps that can be as simple as attaching adhesive Velcro strips to the exterior or as complex as mounting rivets for straps or buckles.

Additional steps that would be appropriate during the development phase of an orthotic device according to the invention for a specific purpose would include f) experimental bench testing the orthotic device produced to evaluate deformation during loading, dimensions, anisotropic stiffness properties, etc.; g) using a comparable finite element analysis software model to analyze deformation from loading and identify alternative materials and geometries to complement the patient's rehabilitation process; h) testing the orthotic device in a physical therapy lab to measure biomechanical differences in gait, sway and center of pressure; i) obtaining the patient's rating of the comfort and usability of the orthotic device; and j) iterating design and geometry changes as necessary based on one or a combination of: patient feedback, biomechanical analysis of the device and its wearer, and measurements taken by embedded sensing elements. These iterations could mean modifying the thickness of the material, the trim lines indicating the edges of the material, locations of the embedded components, density of the material generated during the fabrication process, etc. The sensory data could be monitored remotely from a rehabilitation facility by a medical staff, expanding the effective range of a single facility by treating instrumented orthoses as patient-specific "mobile gait labs."

This production methodology can also be applied to create form-fitting orthotics for other parts of the body and devices in such other areas as custom-fit sockets and prosthetics for amputees; a feedback surgical training tool; and a multi-layer surgical planning tool which duplicates the scanned anatomy of a patient about to undergo surgery (e.g., torso, cranium, heart, knee joint) and monitors the surgeon's practice performance via sensors embedded in the rapidly prototyped organs and skeletal components Moreover, a system embodying the method of the invention can be provided to rehabilitation facilities and hospitals for their own use on-site.

The process described herein does not require that the scanning, data modification, and device fabrication facilities are in close proximity to each other. Each step can be completed remotely from the others since the patient scan data, modification steps, and fabrication instruction files can be communicated over the internet (e.g., via secure server downloads or electronic mail attachments) and, thus, can be separate from each other, which allows for a telemedicine/tele-orthotics treatment for patients.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

FIG. 2B is an image of an AFO device according to the invention showing examples of embedded sensor locations for pressure and temperature;

FIG. 2C is an image of an AFO device according to the invention showing an example of an embedded sensor location for measurement of strain as a predictor of fatigue life and failure mode;

DETAILED DESCRIPTION OF THE INVENTION

As an exemplary patient-specific orthotic device type, a posterior leaf spring AFO that treats drop foot was chosen. A standard AFO was characterized (Type C-90 Superior Posterior Leaf Spring, AliMed, Inc., Dedham, Mass.) and the performance of the orthotic device produced by practice of the method of the invention was compared to this standard device.

Figure 5:
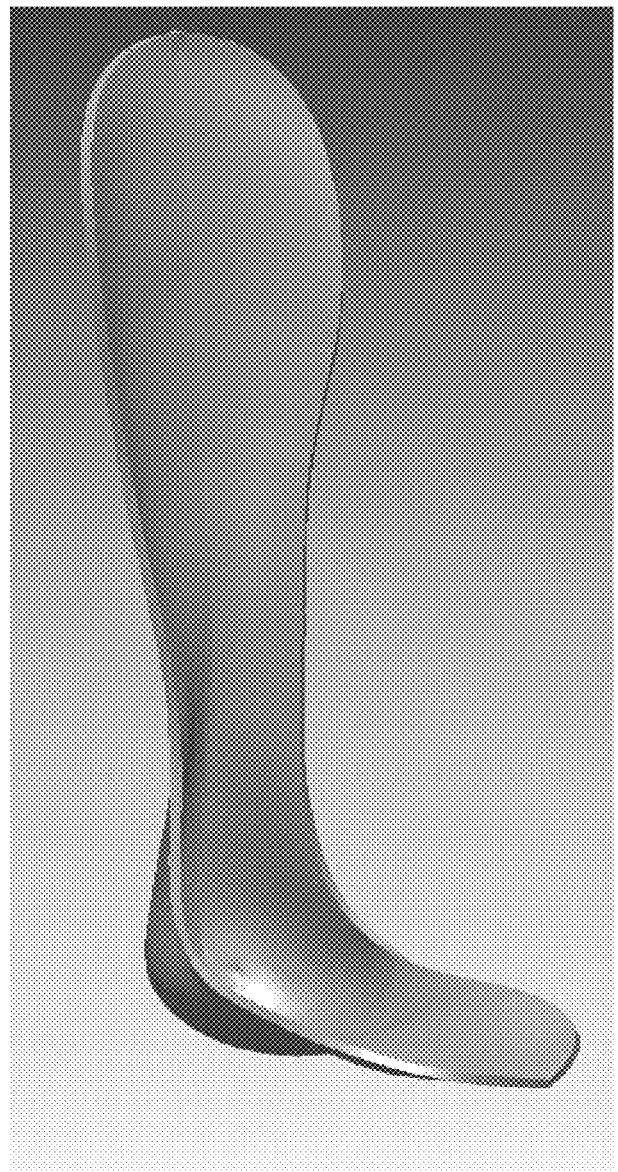
FIG. 5 shows an example of an AFO contour after all digital refinement and preparation operations of practicing the method of the invention have been completed.

The main steps in the method according to the invention are now described. All these steps are general and could be used on any body part. Referring now to FIG. 5, after the body part of the patient in need of the patient-specific orthotic device is identified, the appropriate appendage of the patient is positioned (42) and the external contours of the body part are imaged (43) to obtain a digital image of the freeform surfaces comprising the patient's anatomy in the area of interest using any 3D camera/scanning technology that is capable of creating a full 3D point cloud. This process requires data from the full extent of the body part to be fitted. For an ankle-foot orthotic device, for example, data are collected from below the knee to the heel of the leg and also from the underside of the foot. Depending on the scanning technology selected, individual challenges and techniques exist to obtaining the best quality surface data. Due to the semi-transparent exterior layers of the epidermis, variation in skin tones and presence of hair follicles, assistive scanning devices may be required. In the case of stereoscopic photogrammetry, for example a skin-tight nylon stocking can be wrapped around the anatomy portion to be scanned, which eliminates many of these challenges and normalizes the color tones over the appendage. Use of the skin-tight stocking material also isolates the color ranges for hue and saturation of the white scan surface from extraneous surface data, e.g., the practitioner's gloves and floor. The patient must remain completely still during the scan in order to record the correct surface data. To hold the patient appendage steady during surface capture, it may be necessary to use a fixture or assistive device to the medical practitioner. The scanner itself may be hand held by the practitioner, a medical assistant, or controlled as part of a robotic armature for automated scanning. As a supplement to the method of the invention, the patient's surface data may be captured by making a cast or impression of a specific region of the body part, and this impression may be used as a negative surface representing the patient's anatomy. This kind of supplementation may be necessary, e.g., in order to capture geometry on the side of a joint such as the interior contour of a hand grasping a bar.

Referring again to FIG. 4, the captured data are next modified and manipulated using a range of digital processing tools. These data are in the form of a point cloud, which is a collection of points in three-dimensional space representing the co-ordinates of the scanned surface. Any of the points in the point cloud not matching the hue and saturation range of the scanned surface may now be removed from the scan automatically according to the standards set by the software. Remaining overlapping data points are removed through decimation of the point clouds, and extraneous anomalies like spikes and singularities are removed according to the derivative of the surface curves. When all extraneous data points have been removed, the individual points in the cloud may be connected by triangles to form a surface mesh. Then, according to the instructions of the gait analysis prepared by the medical practitioner, specific surfaces in the mesh from the point cloud may be expanded or contracted to give the final fit more or less freedom of motion against the patient's body. Up to this stage the surfaces comprising the digital model of the patient have contained data of the entire scanned extremity, rather than just the surface area expected to be in direct contact with the patient-specific medical device. The extra data around the contact surfaces is necessary to minimize deviation tolerances during digital manipulation by keeping distances of neighboring points consistent. The extra surfaces are no longer necessary, and are removed when the orthosis contact region is isolated and trimmed using a boundary curve. This is a curve projected onto the surface of the cleaned data points which represents the trimlines where the medical practitioner would normally cut the physical orthosis for the patient.

Once the modified surface has been finalized, it may be offset a distance to provide room for tolerance and compliance with the patient's skin. This offset surface is then thickened into a 3D object along the vectors normal to the surface. The digital model may now have cavities created for the later insertion of embedded components in the final device or may be moved directly to the fabrication step.

Figure 4:
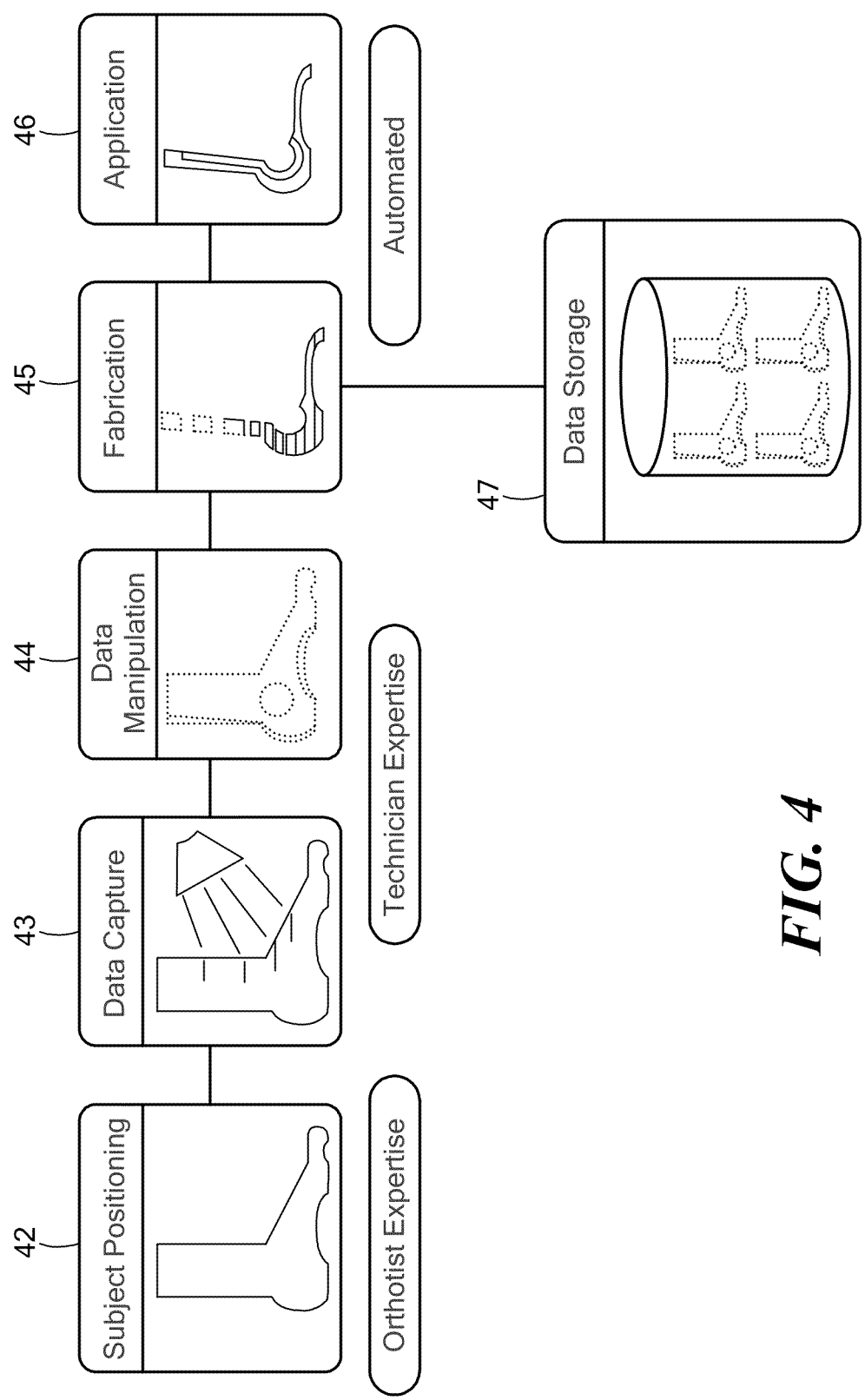
FIG. 4 is a flow diagram showing key procedures in the design and fabrication of an AFO device.

As indicated in FIG. 4, fabrication of the orthotic device using the final digital model (45) can take place using any automated machine capable of following instructions to create 3D surface contours (e.g., layered manufacturing techniques, such as stereolithography; fused deposition modeling; selective laser sintering; CNC milling). The build orientation in the layered fabrication machine is significant because the mechanical properties of the device material will change depending on the build direction. All layered fabrication techniques yield anisotropic materials, which have different material properties depending on the orientation of stress and strain. Currently the weakest build direction in all layered manufacturing processes is in the Z axis (build direction) and so should be noted when orienting a part inside the build envelope. If a part is expected to have certain stiffness properties from a finite element simulation but is oriented differently in the build envelope, then it may deform or yield in unexpected modes. To maintain the highest strength and longest effective lifespan, an AFO, for example, should be build on its side, as if the tibia and navicular are orthogonal with the build direction. Insertion of embedded components may take place either during the build process, following the insertion method described herein as a guideline, or at post-fabrication stages.

Figure 1A:
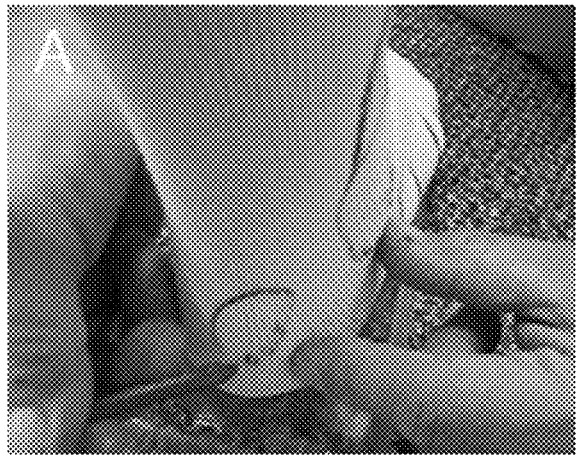
FIGS. 1A-1F are images of a prior art process showing the current fabrication steps necessary to design and fabricate a patient-specific ankle-foot orthotic (AFO) device.
Figure 1B:
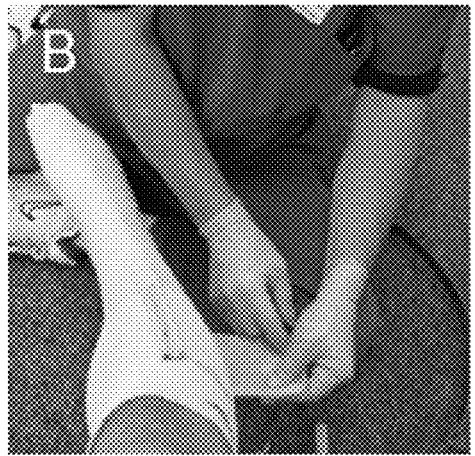
Figure 1C:
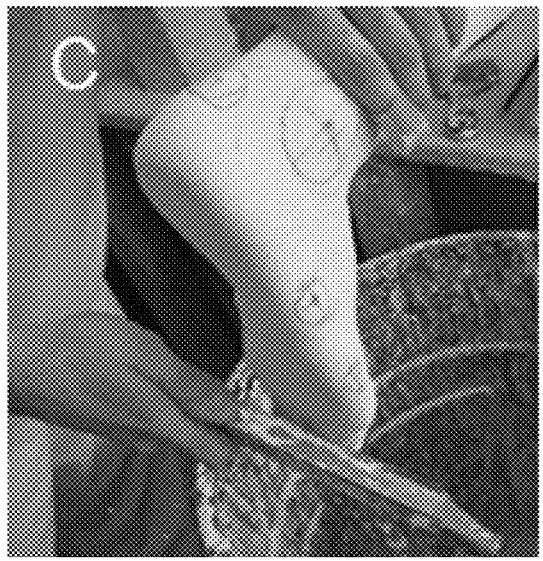
Figure 1D:
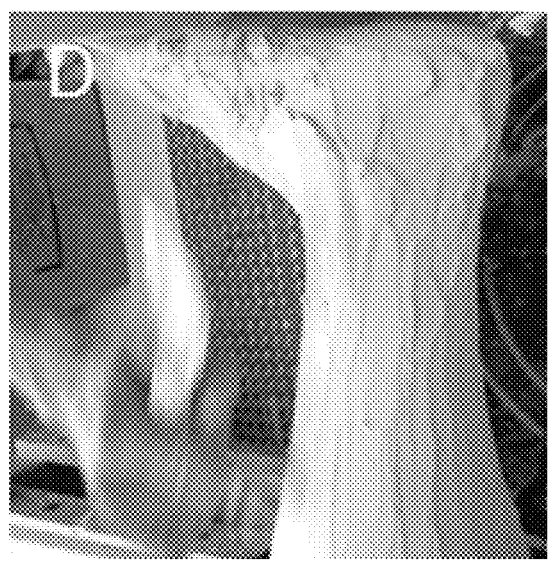
Figure 1E:
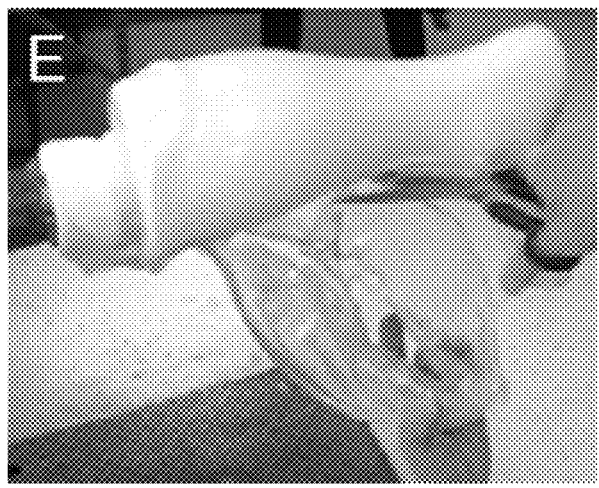
Figure 1F:
Figure 2A:
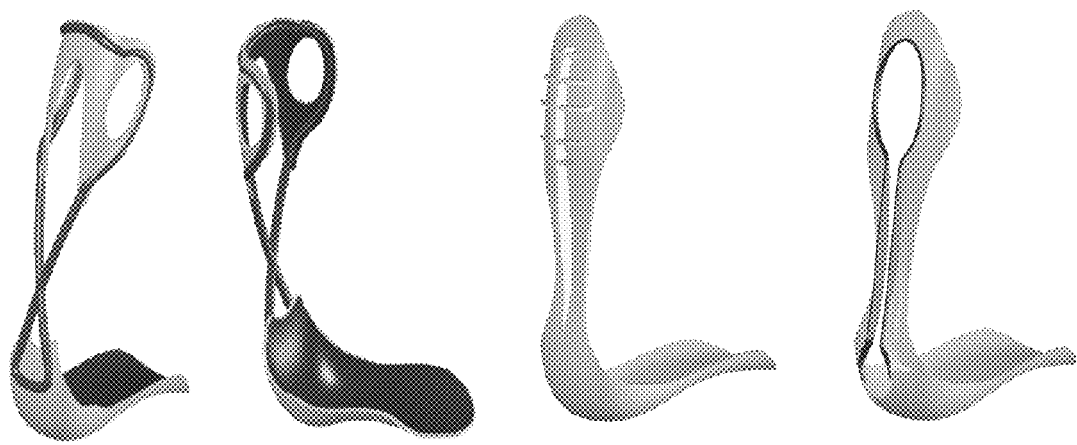
FIG. 2A are images of AFO devices according to the invention with the backing removed to reveal examples of embedded, interchangeable stiffener components of various geometries.

Embedded components (some of which are shown in FIGS. 2A-2D) are meant to diversify the functionality and effectiveness of the device and provide quantifiable feedback to the medical practitioner and patient in the form of sensor data in order to aid the rehabilitation process. Exemplary embedded components and their functions include, e.g., components for sensing (FIG. 2B), for power, for data storage, for data transmission, for electrical muscle stimulation (EMS). For example, strain sensors may be placed at key locations for predicting and tracking the fatigue of the orthotic device and for estimating when the orthotic device might be most likely to break and what the failure mode might be. For an AFO, such sensors are most useful in the region just under the calcaneous, cuboid, and at the base of the fibula as shown in FIG. 2C. A pedometer/accelerometer sensor would be useful for tracking the number of steps taken with the device and for relating a failure mode to distance traveled. Temperature sensors can monitor heat on the skin or friction created by the orthotic device, which can be an indication of skin breakdown in the case of diabetic foot ulcers. Pressure sensors could be used to monitor for swelling in the patient or the distribution of forces during the gait cycle. Any embedded sensor could be implemented in conjunction with a separate instrumentation kit that enabled field deployed gait analysis or actual gate data acquisition at the point of care, which could be in a remote location from the gait lab.

In addition, embedded electrodes with an on-board power supply have the potential to aid rehabilitation by stimulating muscle activity from inside the orthotic device. Recent research has shown that low levels of electrical current can help in the healing process. Magnets have been shown to benefit patients under certain treatment regimes.

Figure 2D:
FIG. 2D is an image of an AFO device according to the invention showing an example of shape memory alloy embedded wires serving as an actuator.
Figure 2D:
Figure 2D:
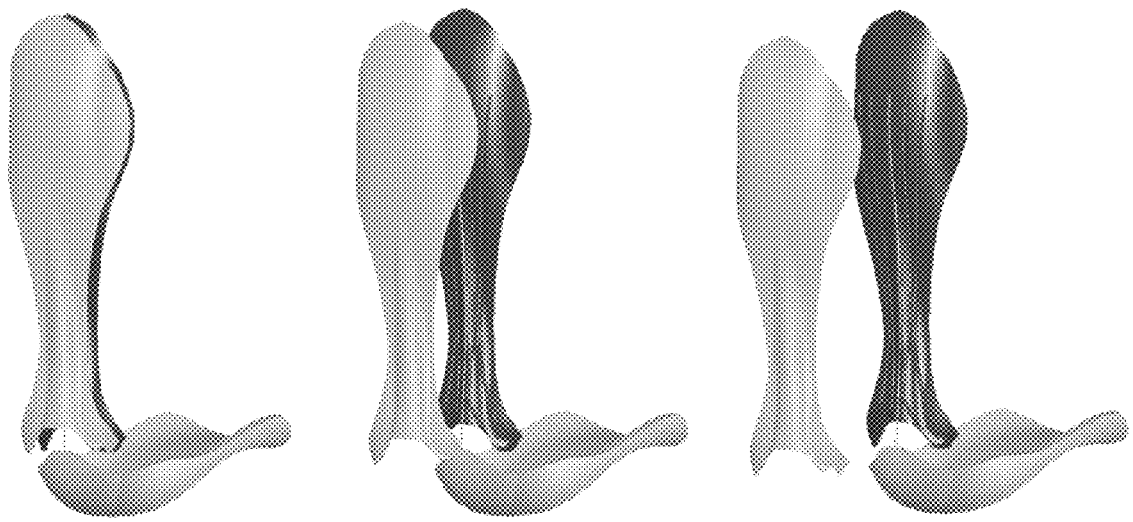

Other exemplary embedded components include actuators (such as electro-active polymers, shape memory alloys (as shown in FIG. 2D), piezoelectric actuators and electromagnetic actuators), which could assist the patient in movement during toe off and also soften forces during heel strike. Microprocessors can permit automatic adjustments and calculations in the orthotic device according to sensor and environmental input. Memory chips can store data from a microprocessor in the orthotic device or can transmit the data wirelessly to a data transmitter/receiver (such as IR, RF, FM or optical), which could be used to transmit information to and from the orthotic device.

Moreover, any patient wearing an instrumented orthosis with embedded data transmission electronics can have a single or team of medical practitioners remotely monitor their rehabilitation gait exercises without physically attending a medical facility. A group of medical experts may monitor a wearer with the capacity to simultaneously conference with engineers and orthotists to recommend redesign constraints to a patient's orthotic device without the need of any two parties to be in the same physical location. Remote monitoring via teleorthotics also allows a practitioner to warn a patient if they are not remaining within their assigned rehabilitation regiment or remind a patient if their orthotic device is reaching the end of its expected safe lifetime.

Interchangeable rods or other components of various geometries, as shown in FIG. 2A, or materials (such as rubber, carbon fiber, aluminum, steel or fiberglass) can be inserted in cavities of the orthotic device, e.g., to change the mechanical characteristics of the device, for example, to stiffen or dampen key regions according the intended patient treatment process. Depending on the treatment regimen and patient range of motion, interchangeable components for an AFO device, for example, could be inserted around the tarsal-metatarsal joints for lateral stability or along the fibula and calcaneous for dorsiflexion/plantarflexion stability support. This would allow for a broader range of orthotic devices all created using the same simple method.

A component can be embedded during the build process by following a basic insertion procedure developed for the production of an articulated robotic hand having embedded components, as described in De Laurentis et al., Assembly Automation, 2004, Vol. 24(4), 394-405. As described in this reference, the proper insertion point for the component was determined by dividing the height (the distance from the platform to the proposed layer of part introduction) by the layer thickness plus one (1) since the machine begins its count at layer one:

$$\text{Insert Level} = \frac{\text{height}}{\text{layer thickness} + 1}$$

It is important to have enough time during the build process for the proper placement of the component into the part being fabricated. This is accomplished by either stopping the machine (not recommended) or by adjusting the z-wait time length at not only the desired layer but also at the previous and successive layers.

In summary, the key points to consider for inserting or embedding component parts are as follows:
(1) correct clearance for part/component types;
(2) proper build orientation;
(3) utilization of support structures;
(4) support configuration and/or style;
(5) elimination or venting of trapped resin volumes;
(6) appropriate selection of components to be embedded;
(7) protection or preparation of sensitive parts to be inserted;
(8) calculation of the right insertion layer level; and
(9) suitable adjustment of the z-wait time.

The same process described above may be used in the surface contour design, development, and fabrication of other patient-specific devices such as haptic computer interfaces (e.g., joysticks, keyboards, mouse); personal electronics (e.g., cell phones, digital camera, remote controller, wearable computer devices); sports equipment (e.g., padded glove, racquet handle, steering wheel, rifle stock, archery bow frame); safety equipment (e.g., safety eyewear, helmet, body padding, wrist guard); ergonomic furniture (e.g., armchair backing, armrest); and tools (e.g., kitchen tools and cutlery, surgical hand tools, power tool gripping surface).

Figure 6:
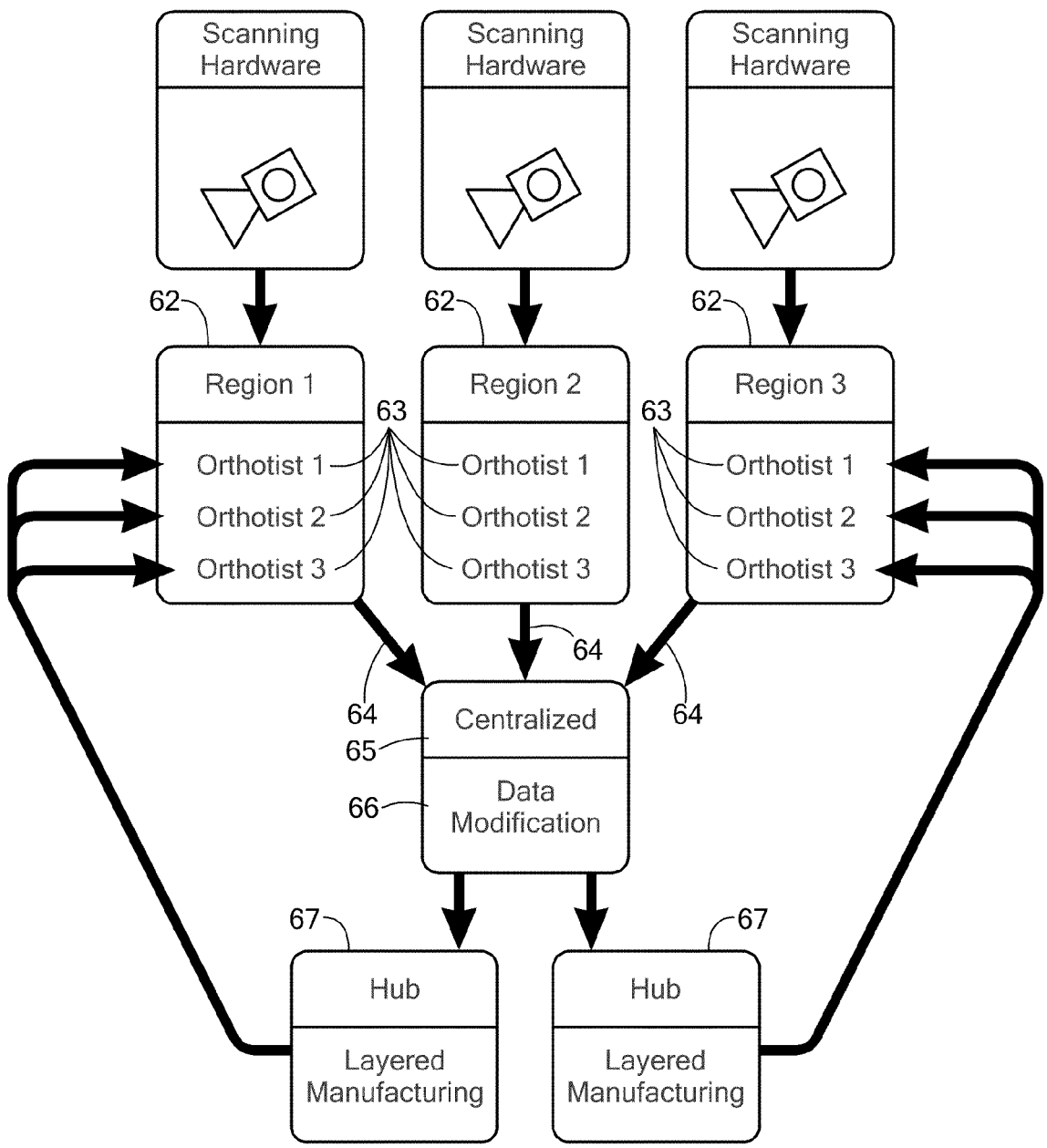
FIG. 6 is a flow diagram showing the telemedicine/tele-orthotics service architecture for distributed locations of patient scanning, digital modification of data, and layered fabrication procedures in the method of the invention.

The process described herein does not require that the scanning, data modification, and device fabrication facilities are in close proximity to each other. Each step can be completed remotely from the others since the patient scan data, modification steps, and fabrication instruction files can be communicated over the internet (e.g., via secure server downloads or electronic mail attachments) and, thus, can be separate from each other, which allows for a telemedicine/tele-orthotics treatment for patients. One embodiment of service architecture to support such remote communication is given in the flow chart of FIG. 6. For example, 3D scanner regional facilities (62) located in different parts of a state each can service several orthotist clinics (63) by scanning patients, e.g., for fit of an AFO. Each scanner regional facility digitally transfers (64) its scan data to a central data processing facility (65) along with a matching instruction file from each orthotist per patient scan. The central data processing facility prepares, modifies, and manipulates the scan data (66) according to the orthotists' instructions and sends the instruction files to several computer automated fabrication facilities for manufacture (67), based on which facility is close to which orthotist. The manufactured AFO device is then returned to the ordering orthotist.

The following examples are presented to illustrate the advantages of the present invention and to assist one of ordinary skill in making and using the same. These examples are not intended in any way otherwise to limit the scope of the disclosure.

Equipment

An exemplary patient-specific orthotic device was manufactured by layered fabrication according to the method of the invention in two prototypes and a final device using different materials and different machines to determine the optimum combination. The common fabrication machine was the Viper Si2 stereolithography (SLA) (Three D Systems, Rock Hill, S.C.). An SLA machine uses a laser beam to sequentially trace the cross sectional slices of an object in a liquid photopolymer resin (e.g. cross sections of an orthosis, organ, anatomical feature). The area of photopolymer that is hit by the laser partially cures into a thin sheet. The platform upon which this sheet sits is then lowered by one layer's thickness (resolution on the order of 0.05 mm) and the laser traces a new cross section on top of the first. These sheets continue to be built one on top of another to create the final three-dimensional shape.

The current AFO that was selected as a model was the Type C-90 Superior Posterior Leaf Spring (Alimed, Inc., Dedham, Mass.) This model geometry, which is available in injection molded polypropylene and a pre-determined range of sizes, offers the subject a full range of plantar and dorsiflexion.

The resin used for prototype 1 and prototype 2a was Accura SI 40 from Three D Systems for the purpose of validating the fabrication surface resolution of SLA. This resin is intended primarily for prototyping and testing of rigid cases and enclosures and is most suitable for high temperature applications. Prototype 2b was built using Somos® 9120 Epoxy Photopolymer (DSM Somos, Elgin, Ill.), which offers superior fatigue properties and strong memory retention. This resin is intended for making medical products and serves as the validation for a medical-grade SLA material. The mechanical properties observed comparing these three materials are listed in Table 1.

TABLE 1

Material Properties Comparison Table

| Description | Unfilled Polypropylene | Accura SI 40 | Somos® 9120 UV |
|---|---|---|---|
| Tensile Strength (MPa) | 31-37.2 | 57.2-58.7 | 30-32 |
| Elongation (%) | 7-13 | 4.8-5.1 | 15-25% |
| Young's Modulus (GPa) | 1.1-1.5 | 2.6-3.3 | 1.2-1.4 |
| Flexural Strength (MPa) | 41-55 | 93.4-96.1 | 41-46 |
| Flexural Modulus (MPa) | 1172-1724 | 2836-3044 | 1310-1455 |

The 3D scans used for the prototypes were obtained by use of a 3D FaceCam 500 (Genex Technologies, Inc., Bethesda, Md.). This 3D scanner uses stereoscopic photogrammetry to capture a 3D surface by triangulating the reflection of a projected scattered pattern of colored light. The field of view allows a 3D resolution of 307,200 (640×480) data points of information. This technology is able to capture images for both the geometry and the texture of the desired body part of the subject that is being scanned. The data that is received from the camera is in the form of a full 3D point cloud with all contours greater than 0.5 mm.

Scanning Methods

In order to get the best quality data from the 3D scans, a specific process was used to capture and securely hold the patient's ankle-foot complex. The scanning operation was broken down into 3 images of the ankle region with the patient in a seated incline position leaning forward. Other orientations are possible but this was the best combination of patient comfort, minimal number of scans, and ease to position the ankle into the necessary pose of "subtalar neutral." The patient's leg was covered with a skin-tight nylon sock to create a uniform surface to scan and counteract inherent scanning difficulties like hair follicles, specularity, and non-uniform skin tone. This step is a valuable aid in the software processes that follow because it normalized the scan surface.

The 3D camera (FaceCam) was placed on level with the part of the body that required an orthotic device. The FaceCam was placed at 70 cm from the target body part for optimal focal range.

Figure 3:
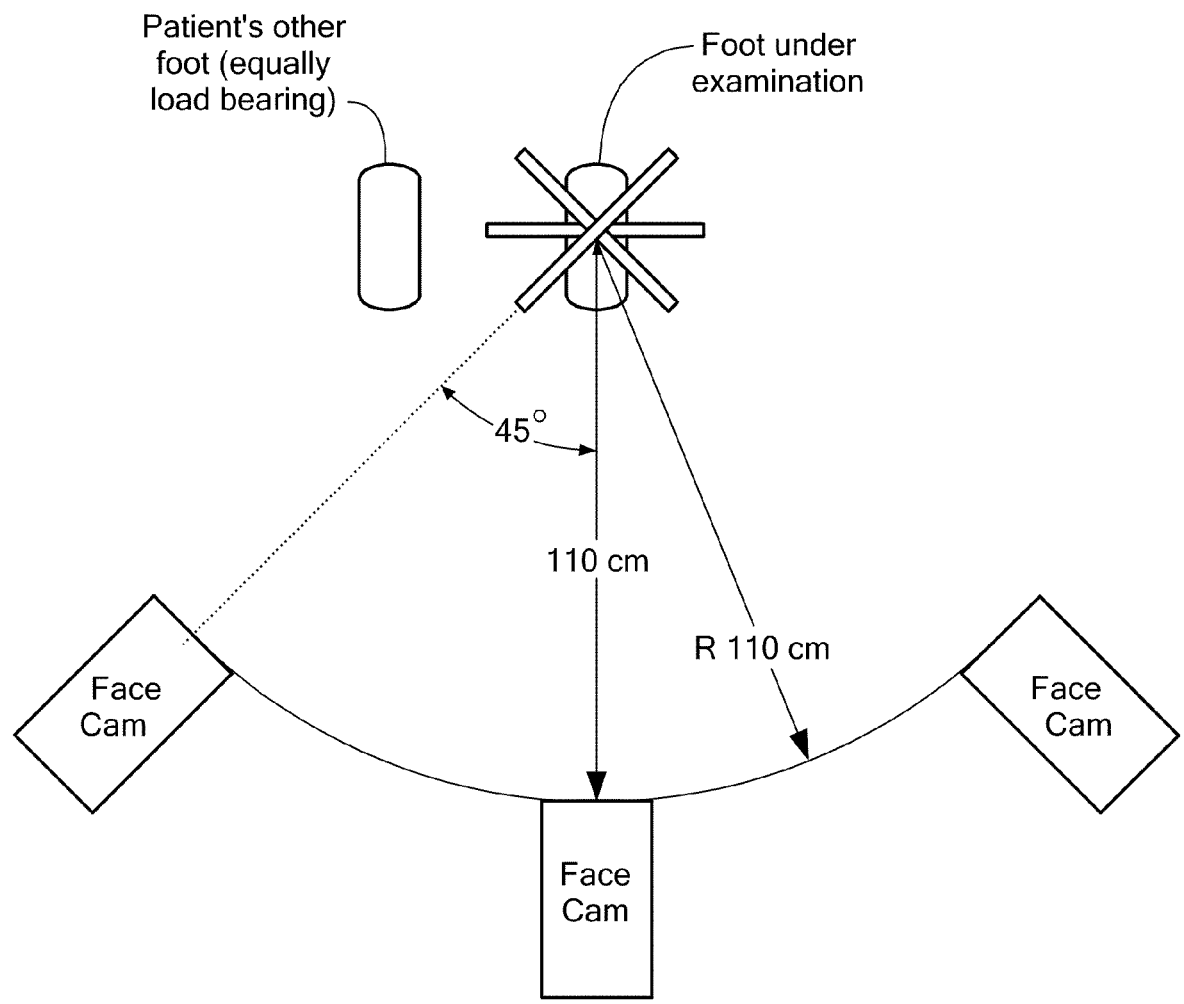
FIG. 3 is a diagram representing the scanning procedure for the ankle-foot region of a patient in need of a patient-specific ankle-foot orthotic device during practice of the method of the invention.

For an ankle-foot orthotic device such as described herein, the patient should be leaning forward at an incline exposing the ankle and leg. FIG. 3 shows the position of the camera for each of the scans of the ankle area while load bearing. The 3D scanner should be placed at the same level as the patient's ankle cup and 70 cm directly behind the posterior of the leg. The first scan is taken from this position. The next two scans are taken from −45 and 45 degrees from the posterior scan, as illustrated in FIG. 3.

Software Procedure

The software used to clean, smooth and combine the scans to a workable CAD model was RapidForm2004 (Rapidform, Inc. Sunnyvale, Calif.). After the data for the scans were moved into the RapidForm software, extraneous data for the background and floor were removed based on the color of the patient's leg and the background. The individual scans were cleaned to remove spikes and anomalies as well as to smooth the contours and fill holes in the mesh for any missing data points. As few modifying steps as possible were used so as to preserve the integrity of the original scans while at the same time removing extraneous data. To merge individual meshes into a single mesh, it is necessary that the meshes overlap slightly by sharing common points. The algorithms used by Rapidform require common points as a reference to align the meshes.

After the cleaning and merging procedures were carried out, the surfaces of the digital model which will be the patient contact interface (e.g., edges of the orthotic device) were isolated and cut using a boundary curve. The final surface was offset and thickened according to the guidelines described herein. Once completed, the final model was exported from RapidForm2004 as a .STL file for use in a rapid prototyping machine, e.g., the Viper Si2 SLA machine.

Prototype 1

The digital model for prototype 1 was created to prove the viability of the technology and the processes used by evaluating the resolution of the freeform surfaces comprising the contours on the anterior part of the leg. This prototype was successfully fabricated using the Viper SLA machine and preliminary data from the patient's leg. The build cycle consisted of 1643 layers of resin, and was built in a total time of 21.07 hours. The data for the bottom of the foot were not available for this prototype, so underside surfaces were added in synthetically from the RapidForm2004 program using the hole-filling tool. Prototype 1 proved that the process could produce a reasonable end surface for a product, but showed that further refinement of the scan surface data would be required and illustrated the need for a number of scanning positions to collect the appropriate data.

Prototype 2

In prototype 2, bottom of the foot data were captured to a new 3D scan to show that merging of data from the bottom of the foot was possible. This prototype digital model was fabricated with two different SLA materials: Accura SI 40 (Prototype 2a) and Somos® 9120 (Prototype 2b). Due to restrictions of the built platform of the Viper, prototype 2a had to be fabricated in an inclined build orientation. This build cycle consisted of 2,269 layers of resin and was built in a total time of 16.7 hours.

The prototype 2b digital model was sent to a commercial RP service vendor to be built using Somos 9120 resin (prototype 2b). FIG. 5 shows the final computer model for prototype 2 that was sent to be built. Both fabricated versions of Prototype 2 proved that with the included bottom of the foot data, the fit to the patient was excellent.

Table 2 is a comparison between the physical properties of the standard polypropylene AFO and prototype 2(a&b), whose dimensions closely matched those of the polypropylene AFO but weighed 21% less.

TABLE 2

Dimensions of Final Prototype

| Dimensions (mm) | Prototype 2 | Non Patient-Specific Polypropylene AFO |
|---|---|---|
| Length | 295 | 305 |
| Width | 70 | 60 |
| Depth | 145 | 156 |
| Weight (grams) | 2a (Accura 40) = 92<br>2b (Somos 9120) = 85 | 117 |

Once the final prototype mechanical analysis was completed, testing and validation of its design while on a patient was performed.

Testing and Validation

Gait evaluations were conducted of a single healthy subject at Spaulding Rehabilitation Hospital, Boston, Mass. using a Vicon motion capture system. A healthy subject's gait cycle was used as a control to evaluate gait deviations without an AFO compared to gait with a standard (polypropylene) AFO and the AFOs fabricated according to the method of the invention. Each of the three AFOs was fitted to the right leg of the subject during four separate walking tests to determine the effect, if any, of the orthotic device on a subject's normal gait: (1) with sneakers and no AFO (No AFO); (2) with the standard polypropylene AFO (Standard AFO); (3) with the rigid AFO made with the Accura 40 resin (Prototype 2a), and (4) with the flexible AFO made from the Somos® 9120 resin (Prototype 2b).

To characterize the gait pattern of the subject reflective markers placed with on the following specific anatomical landmarks of the subject's pelvis, and knee, ankle and foot of each leg. Additional markers were also rigidly attached to wands and placed over the mid-femur and mid-shank. The subject was instructed to walk along a 20 foot walkway at a comfortable speed for all trials. Results from this type of study can be used by physicians in the prescription and evaluation of orthotic and prosthetic devices as well as for other clinical applications requiring the analysis of movement patterns during ambulation. The normal gait analysis results are gathered in order to have baseline comparison data. Comparing the three different AFOs allows one to establish how the patient specific AFO perform compared to the standard AFO.

For each setup, data were gathered from both the left and the right side. The data taken for each side were broken down into the sagittal plane and the coronal plane. Pelvic, hip, knee and ankle data were taken for each plane, as listed in Table 3.

TABLE 3

Biomechanical Test Data

| Plane | Pelvic | Hip | Knee | Ankle |
|---|---|---|---|---|
| Sagittal | Tilt | Flexion/Extension Moment Power | Flexion/Extension Moment Power | Dorsi/Plantar Moment Power |
| Coronal | Obliquity | Abduction/Adduction Moment | Abduction/Adduction Moment | Abduction/Adduction Moment |

Temporal parameters were examined across all the experimental conditions to test whether different AFO implementations had an effect on the temporal characteristics of ambulation. These parameters include cadence, step length, step time, stride length, stride time, and walking speed. Additionally, the percent of the gait cycle spent in double support and the timing of foot off, opposite foot contact and opposite foot off were calculated. These characteristics are compared in Table 4 for four gait conditions (no AFO, standard AFO, rigid final prototype, and flexible final prototype).

TABLE 4

Mean (±SD) spatiotemporal gait parameters of the right side for the 4 AFO conditions.

| Parameter | No AFO | Standard AFO | Rigid RP AFO (Prototype 2a) | Flexible RP AFO (Protoype 2b) |
|---|---|---|---|---|
| Walking speed (m/s) | 1.49 ± 0.05 | 1.46 ± 0.02 | 1.50 ± 0.06 | 1.44 ± 0.05 |
| Step length (m) | 0.79 ± 0.02 | 0.79 ± 0.01 | 0.82 ± 0.03 | 0.79 ± 0.03 |
| Double support time (s) | 0.22 ± 0.02 | 0.24 ± 0.01 | 0.23 ± 0.01 | 0.24 ± 0.01 |

When the subject performed each of the testing exercises wearing each of the AFOs to be tested, the results compared to no AFO showed that initial contact with the floor was made with the foot in a more neutral position, which allowed for more plantarflexed initial contact. This result is most likely due to the AFOs being made when the subject's foot was set in subtaylor neutral position, i.e., 0° dorsiflexion, and wearing the device then decreased range of motion for platarflexion. There was more range of motion (RoM) for the standard polypropylene AFO vs. AFOs made by the method of the invention. This may be due to greater compliance and flexability of polypropylene or to a poorer fit of the standard AFO around the foot and ankle of the subject. A poorer fitting AFO will likely allow more movement at the ankle joint, which it is meant to control, because it is not in sufficient contact with all of the bony protuberances around the calcaneus and cuboid.

Just before toe-off, an AFO is meant to assist with the progression of the lower leg over the foot by stabilizing dorsiflexion at the ankle. The standard polypropylene AFO allows more RoM during this phase compared to the AFOs according to the invention, which perform similarly. This greater RoM is due to a combination of greater plantarflexion and also greater dorsiflexion during gait, derived from the specificity of the fit of the AFO according to the invention to the subject.

Overall, results showed that the patient-specific AFOs performed as well as the standard AFO for RoM studies, and in some respects outperformed them for securing the ankle-foot complex during gait.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for computer-controlled fabrication of a patient-specific orthotic device, said method comprising, in the order given, the steps of:

identifying a body part of a patient in need of a patient-specific orthotic device comprising an embedded component selected from components for sensing, components for power, components for data storage, components for data transmission and components for electrical muscle stimulation;

imaging the external contours of said body part to obtain a three-dimensional (3D) point cloud of said part;

electronically manipulating said point cloud of said body part to incorporate revisions from a medical practitioner and to obtain a computer model of at least one part of said patient-specific orthotic device with the embedded component;

converting data comprising said orthotic device computer model into an instruction file accommodating for the embedded component for computer-controlled layered deposition fabrication of said at least one part of said patient-specific orthotic device; and transferring said instruction file to an automated fabrication machine for direct computer-controlled fabrication of said at least one part of said patient-specific orthotic device with the embedded component on an automated fabrication machine capable of following computer instructions to create 3D surface contours.

2. The method of claim 1, wherein the product of said computer-controlled fabrication step is a prototype for said at least one part of said patient-specific orthotic device.

3. The method of claim 1, wherein the product of said computer-controlled fabrication step is a final product said at least one part of said patient-specific orthotic device.

4. The method of claim 1 further comprising the step of programming specifications for said orthotic device into a computer, wherein, in said programming step, said specifications are selected from the group consisting of type of orthotic device, material of orthotic device, and geometry of orthotic device.

5. A method for computer-controlled fabrication of a patient-specific ankle-foot orthotic (AFO) device, said method comprising, in the order given, the steps of:
- identifying an ankle-foot complex of a patient in need of a patient-specific AFO device comprising an embedded component selected from components for sensing, components for power, components for data storage, components for data transmission and components for electrical muscle stimulation;
- imaging the external contours of said ankle-foot complex to obtain a three-dimensional (3D) point cloud of said ankle-foot complex;
- electronically manipulating said point cloud of said ankle-foot complex to incorporate revisions from a medical practitioner and to obtain a computer model of at least one part of said patient-specific AFO device with the embedded component;
- converting data comprising said AFO device computer model into an instruction file accommodating for the embedded component for computer-controlled layered deposition fabrication of said at least one part of said patient-specific AFO device; and
- transferring said instruction file to an automated fabrication machine for direct computer-controlled fabrication of said at least one part of said patient-specific AFO device with the embedded component using one or more layered manufacturing techniques implemented with an automated fabrication machine capable of following computer instructions to create 3D surface contours.

6. The method of claim 5, further including positioning the ankle-foot complex into a desired pose prior to imaging the external contours of the ankle-foot complex.

7. The method of claim 6, wherein the desired pose is subtalar neutral.

8. The method of claim 6, wherein one or more of the (i) imaging, (ii) electronically manipulating and (iii) carrying out computer-controlled fabrication steps are performed in a remote location with respect to one another.

9. A method for computer-controlled fabrication of a patient-specific ankle-foot orthotic (AFO) device, said method comprising, in the order given, the steps of:
- identifying an ankle-foot complex of a patient in need of a patient-specific AFO device comprising an embedded component selected from components for sensing, components for power, components for data storage, components for data transmission and components for electrical muscle stimulation;
- positioning the ankle-foot complex into a desired pose;
- imaging the external contours of said ankle-foot complex to obtain a three-dimensional (3D) point cloud of said ankle-foot complex;
- electronically manipulating said point cloud of said ankle-foot complex to incorporate revisions from a medical practitioner and to obtain a computer model of at least one part of said patient-specific AFO device with the embedded component;
- converting data comprising said AFO device computer model into an instruction file accommodating for the embedded component for direct computer-controlled fabrication of said at least one part of said patient-specific AFO device; and
- carrying out computer-controlled fabrication of said at least one part of said patient-specific AFO device with the embedded component using one or more layered manufacturing techniques implemented with an automated layered deposition fabrication machine capable of following computer instructions to create 3D surface contours;
- wherein one or more of the (i) imaging, (ii) electronically manipulating and (iii) carrying out computer-controlled fabrication steps are performed in a remote location with respect to one another.

10. The method of claim 1, wherein electronically manipulating said point cloud of said body part includes providing extra data near surfaces represented by the point cloud that are in direct contact with the patient-specific orthotic device.

11. The method of claim 1, wherein the revisions from a medical practitioner include gait analysis information.

12. The method of claim 1, wherein the medical practitioner includes an orthotist.

13. The method of claim 1, wherein the medical practitioner is an orthotics professional.

14. The method of claim 13, wherein the orthotics professional is overseen by an orthotist.

15. The method of claim 1, wherein the medical practitioner is a collaboration of an orthotist and an engineer.

16. The method of claim 1, wherein the computer-controlled layered deposition fabrication is selected from stereolithography, fused deposition modeling and selective laser sintering.

17. The method of claim 1, wherein the embedded component comprises a strain sensor.

* * * * *